US006992091B2

(12) United States Patent  
Duncia et al.

(10) Patent No.: US 6,992,091 B2
(45) Date of Patent: Jan. 31, 2006

(54) N-UREIDOALKYL-PIPERIDINES AS MODULATORS OF CHEMOKINE RECEPTOR ACTIVITY

(75) Inventors: John V. Duncia, Newtown, PA (US); Daniel S. Gardner, Furlong, PA (US); Joseph B. Santella, Springfield, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 250 days.

(21) Appl. No.: 10/660,347

(22) Filed: Sep. 11, 2003

(65) Prior Publication Data

US 2004/0082616 A1    Apr. 29, 2004

Related U.S. Application Data

(60) Provisional application No. 60/410,198, filed on Sep. 12, 2002.

(51) Int. Cl.
*A61K 31/445*    (2006.01)
*C07D 401/04*    (2006.01)

(52) U.S. Cl. ....................... 514/326; 546/210
(58) Field of Classification Search ............... 514/326; 546/210
See application file for complete search history.

(56) References Cited

U.S. PATENT DOCUMENTS

| 5,668,151 | A | 9/1997 | Poindexter et al. .......... 514/318 |
| 6,323,334 | B1 * | 11/2001 | Kingsbury et al. ......... 536/23.5 |
| 6,331,541 | B1 | 12/2001 | Ko et al. .................. 514/237.2 |
| 6,339,087 | B1 | 1/2002 | Gong et al. ............. 514/252.12 |
| 6,486,180 | B1 | 11/2002 | Ko et al. ..................... 514/331 |
| 6,638,950 | B2 | 10/2003 | Duncia et al. .............. 514/326 |
| 6,770,650 | B2 * | 8/2004 | Gong et al. ............. 514/253.01 |

FOREIGN PATENT DOCUMENTS

| WO | WO 93/06108 | 4/1993 |
| WO | WO 94/22846 | 10/1994 |
| WO | WO 95/13069 | 5/1995 |
| WO | WO 97/27752 | 8/1997 |
| WO | WO 98/25604 | 6/1998 |
| WO | WO 99/04794 | 2/1999 |
| WO | 903349 | 3/1999 |
| WO | WO 00/35453 | 6/2000 |

OTHER PUBLICATIONS

Mammen et al. "Preparation of biphenyl derivatives . . . " CA 141:225161 (2004).*

* cited by examiner

*Primary Examiner*—Celia Chang
(74) *Attorney, Agent, or Firm*—Mary VanAtten

(57) ABSTRACT

The present application describes N-ureidoalkyl piperidines as modulators of chemokine receptors, or pharmaceutically acceptable salt forms thereof, useful for the prevention of asthma and other allergic diseases.

7 Claims, No Drawings

US 6,992,091 B2

N-UREIDOALKYL-PIPERIDINES AS MODULATORS OF CHEMOKINE RECEPTOR ACTIVITY

CROSS REFERENCE TO RELATED APPLICATIONS

The present application claims the priority benefit of U.S. Provisional Application No. 60/410,198, filed Sep. 12, 2002, which is expressly incorporated fully herein by reference.

FIELD OF THE INVENTION

This invention relates generally to modulators of chemokine receptor activity, pharmaceutical compositions containing the same, and methods of using the same as agents for treatment and prevention of inflammatory diseases such as asthma and allergic diseases, as well as autoimmune pathologies such as rheumatoid arthritis and atherosclerosis.

BACKGROUND OF THE INVENTION

Chemokines are chemotactic cytokines, of molecular weight 6–15 kDa, that are released by a wide variety of cells to attract and activate, among other cell types, macrophages, T and B lymphocytes, eosinophils, basophils and neutrophils (reviewed in Luster, New Eng. J. Med., 338, 436–445 (1998) and Rollins, Blood, 90, 909–928 (1997)). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (−1,−2, and -3) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seven-transmembrane-domain proteins (reviewed in Horuk, Trends Pharm. Sci., 15, 159–165 (1994)) which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns: CCR-1 (or "CKR-1" or "CC-CKR-1") [MIP-1α, MCP-3, MCP-4, RANTES] (Ben-Barruch, et al., Cell, 72, 415–425 (1993), Luster, New Eng. J. Med., 338, 436–445 (1998)); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo et al., Proc. Natl. Acad. Sci. USA, 91, 2752–2756 (1994), Luster, New Eng. J. Med., 338, 436–445 (1998)); CCR-3 (or "CKR-3" or "CC-CKR-3") [eotaxin-1, eotaxin-2, RANTES, MCP-3, MCP-4] (Combadiere, et al., J. Biol. Chem., 270, 16491–16494 (1995), Luster, New Eng. J. Med., 338, 436–445 (1998)); CCR-4 (or "CKR-4" or "CC-CKR-4") [TARC, MIP-1α, RANTES, MCP-1] (Power et al., J. Biol. Chem., 270, 19495–19500 (1995), Luster, New Eng. J. Med., 338, 436–445 (1998)); CCR-5 (or "CKR-5" OR "CC-CKR-5") [MIP-1α, RANTES, MIP-1β] (Sanson, et al., Biochemistry, 35, 3362–3367 (1996)); CCR-6 (or "CKR-6" or "CC-CKR-6") [LARC] (Baba et al., J. Biol. Chem., 272, 14893–14898 (1997)); CCR-7 (or "CKR-7" or "CC-CKR-7") [ELC] (Yoshie et al., J. Leukoc. Biol. 62, 634–644 (1997)); CCR-8 (or "CKR-8" or "CC-CKR-8") [I-309, TARC, MIP-1β] (Napolitano et al., J. Immunol., 157, 2759–2763 (1996), Bernardini et al., Eur. J. Immunol., 28, 582–588 (1998)); and CCR-10 (or "CKR-10" or "CC-CKR-10") [MCP-1, MCP-3] (Bonini et al, DNA and Cell Biol., 16, 1249–1256 (1997)). Two recent reviews of chemokine receptors can be found at (i) A. Zlotnik and O. Yoshi, Immunity 2000, 12, 121–127; and (ii) P. H. Carter, Current Opinion in Chemical Biology 2002, 6, 510–52.

In addition to the mammalian chemokine receptors, mammalian cytomegaloviruses, herpesviruses and poxviruses have been shown to express, in infected cells, proteins with the binding properties of chemokine receptors (reviewed by Wells and Schwartz, Curr. Opin. Biotech., 8, 741–748 (1997)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as coreceptors for the infection of mammalian cells by microbes as with, for example, the human immunodeficiency viruses (HIV).

Chemokine receptors have been implicated as being important mediators of inflammatory, infectious, and immunoregulatory disorders and diseases, including asthma and allergic diseases, as well as autoimmune pathologies such as rheumatoid arthritis and atherosclerosis. For example, the chemokine receptor CCR-3 plays a pivotal role in attracting eosinophils to sites of allergic inflammation and in subsequently activating these cells. The chemokine ligands for CCR-3 induce a rapid increase in intracellular calcium concentration, increased expression of cellular adhesion molecules, cellular degranulation, and the promotion of eosinophil migration. Accordingly, agents which modulate chemokine receptors would be useful in such disorders and diseases. In addition, agents which modulate chemokine receptors would also be useful in infectious diseases such as by blocking infection of CCR3 expressing cells by HIV or in preventing the manipulation of immune cellular responses by viruses such as cytomegaloviruses.

A substantial body of art has accumulated over the past several decades with respect to substituted piperidines, piperizinones and pyrrolidines. These compounds have implicated in the treatment of a variety of disorders.

WO 98/25604 describes spiro-substituted azacycles which are useful as modulators of chemokine receptors:

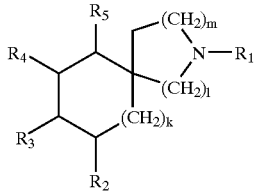

wherein $R_1$ is $C_{1-6}$ alkyl, optionally substituted with functional groups such as —$NR^6CONHR^7$, wherein $R^6$ and $R^7$ may be phenyl further substituted with hydroxy, alkyl, cyano, halo and haloalkyl. Such spiro compounds are not considered part of the present invention.

WO 95/13069 is directed to certain piperidine, pyrrolidine, and hexahydro-1H-azepine compounds of general formula:

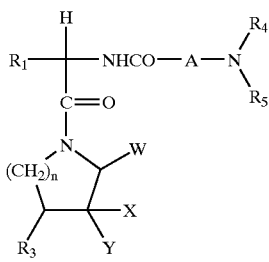

wherein A may be substituted alkyl or Z-substituted alkyl, with Z=$NR_{6a}$ or O. Compounds of this type are claimed to promote the release of growth hormone in humans and animals.

WO 93/06108 discloses pyrrolobenzoxazine derivatives as 5-hydroxytryptamine (5-HT) agonists and antagonists:

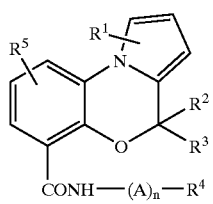

wherein A is lower alkylene and $R^4$ may be phenyl optionally substituted with halogen.

U.S. Pat. No. 5,668,151 discloses Neuropeptide Y (NPY) antagonists comprising 1,4-dihydropyridines with a piperidinyl or tetrahydropyridinyl-containing moiety attached to the 3-position of the 4-phenyl ring:

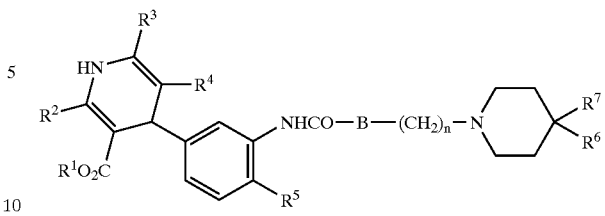

wherein B may be NH, $NR^1$, O, or a bond, and $R^7$ may be substituted phenyl, benzyl, phenethyl and the like.

Patent publication EP 0 903 349 A2 discloses CCR-3 receptor antagonists comprising cyclic amines of the following structure:

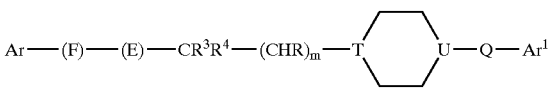

wherein T and U may be both nitrogen or one of T and U is nitrogen and the other is carbon and E may be —$NR^6CONR^5$— and others.

WO 97/27752 discloses compounds of the general formula:

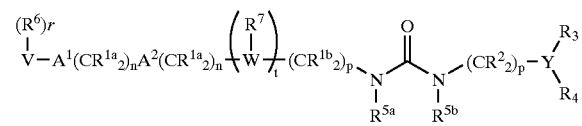

wherein W may be a pyrazole ring. These compounds are claimed to treat cancer as inhibitors of farnesyl-protein transferase.

WO 99/04794 is directed towards modulators of chemokine activity having the general formula:

wherein the claimed compounds are exclusively para-substituted piperidines.

WO 94/22846 discloses compounds having the general formula:

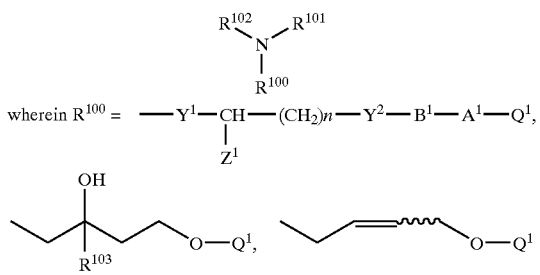

-continued

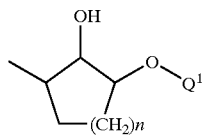

and optionally having the $R^{101}$ and $R^{102}$ connected to form a heterocycle ring. These compounds are disclosed as agents for sensitizing tumor cells or as anti cancer agents.

WO 00/35453 discloses having the general formula

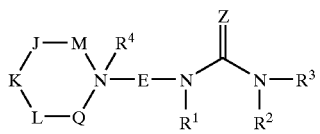

The examples shown in WO 00/35453 are not considered to be part of the present invention The prior art does not disclose nor suggest the unique combination of structural fragments which embody these novel N-ureidoalkyl-piperidines as having activity toward the chemokine receptors.

SUMMARY OF THE INVENTION

Accordingly, one aspect of the present invention is to provide novel agonists or antagonists of CCR-3, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating inflammatory diseases and allergic disorders comprising administering to a host in need of such treatment a therapeutically effective amount of at least one of the compounds of the present invention or a pharmaceutically acceptable salt or prodrug form thereof.

The present invention provides novel N-ureidoalkyl-piperidines for use in therapy.

The present invention provides the use of novel N-ureidoalkyl-piperidines for the manufacture of a medicament for the treatment of allergic disorders.

These and other features, which will become apparent during the following detailed description, have been achieved by the inventors' discovery that compounds of formula (I):

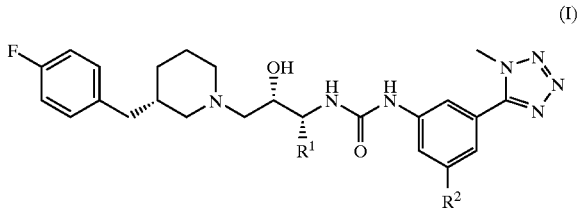

or stereoisomers or pharmaceutically acceptable salts thereof, wherein $R^1$ and $R^2$ are defined below, are effective modulators of chemokine activity.

DETAILED DESCRIPTION OF EMBODIMENTS OF THE PRESENT INVENTION

[1] Thus, in a first embodiment, the present invention provides novel compounds of formula (I):

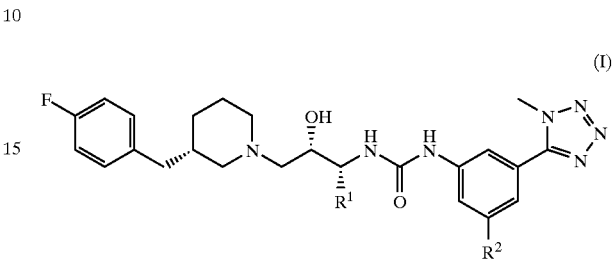

or a pharmaceutically acceptable salt form thereof, wherein
$R^1$ is selected from methyl; and
$R^2$ is selected from H, methyl, and ethyl.

In another embodiment, the present invention provides compounds of formula (I), wherein
$R^2$ is H.
In another embodiment, the present invention provides compounds of formula (I), wherein
$R^2$ is methyl.
In another embodiment, the present invention provides compounds of formula (I), wherein
$R^2$ is ethyl.

[5] In another embodiment, the present invention provides compounds of formula (I), wherein the compound is selected from:
N-[3-ethyl-5-(1-methyl-1H-tetraazol-5-yl)phenyl]-N'-{(1R,2S)-3-[(3S)-3-(4-fluorobenzyl)-1-piperidinyl]-2-hydroxy-1-methylpropyl}urea;
N-{(1R, 2S)-3-[(3S)-3-(4-fluorobenzyl)-1-piperidinyl]-2-hydroxy-1-methylpropyl}-N'-[3-(1-methyl-1H-tetraazol-5-yl)phenyl]urea; and
N-{(1R,2S)-3-[(3S)-3-(4-fluorobenzyl)-1-piperidinyl]-2-hydroxy-1-methylpropyl}-N'-[3-methyl-5-(1-methyl-1H-tetraazol-5-yl)phenyl]urea.

In another embodiment, the present invention provides a pharmaceutical composition, comprising a pharmaceutically acceptable carrier and a therapeutically effective amount of a compound of the present invention.

In another embodiment, the present invention provides a method for modulation of chemokine receptor activity comprising administering to a patient in need thereof a therapeutically effective amount of a compound of the present invention.

In another embodiment, the present invention provides pharmaceutical composition comprising a pharmaceutically acceptable carrier and a therapeutically effective amount of a compound of the present invention or a pharmaceutically acceptable salt thereof.

In another embodiment, the present invention provides a method of modulation of chemokine receptor activity which comprises contacting a CCR3 receptor with an effective inhibitory amount of the compound.

In another embodiment, the present invention provides a method for treating inflammatory disorders comprising administering to a patient in need thereof a therapeutically effective amount of a compound of the present invention, or a pharmaceutically acceptable salt thereof.

In another embodiment, the present invention provides a method for treating disorders selected from asthma, allergic rhinitis, atopic dermatitis, inflammatory bowel diseases, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, HIV infection, cystic fibrosis, Churg-Strauss syndrome, lymphoma, Hodgkin's disease, and colonic carcinoma.

In another embodiment, the present invention provides a method for treating disorders selected from asthma, allergic rhinitis, atopic dermatitis, and inflammatory bowel diseases.

In another embodiment, the present invention provides a method for treating asthma.

In another embodiment, the present invention provides a method for treating allergic rhinitis.

In another embodiment, the present invention provides a method for treating atopic dermatitis.

In another embodiment, the present invention provides a method for treating inflammatory bowel diseases.

In another embodiment, the present invention provides novel N-ureidoalkyl-piperidines compounds for use in therapy.

In another embodiment, the present invention provides the use of novel N-ureidoalkyl-piperidines compounds for the manufacture of a medicament for the treatment of HIV infection.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^a$) occurs more than one time in any constituent or formula for a compound, its definition at each occurrence is independent of its definition at every other occurrence. Thus, for example, if a group is shown to be substituted with 0–2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl. $C_{1-8}$ alkyl, is intended to include $C_1$, $C_2$, $C_3$, $C_4$, $C_5$, $C_6$, $C_7$, and $C_8$ alkyl groups. "Alkenyl" is intended to include hydrocarbon chains of either a straight or branched configuration and one or more unsaturated carbon-carbon bonds which may occur in any stable point along the chain, such as ethenyl, propenyl, and the like. "Alkynyl" is intended to include hydrocarbon chains of either a straight or branched configuration and one or more unsaturated triple carbon-carbon bonds which may occur in any stable point along the chain, such as ethynyl, propynyl, and the like. "$C_{3-6}$ cycloalkyl" is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptyl in the case of $C_7$ cycloalkyl. $C_{3-6}$ cycloalkyl, is intended to include $C_3$, $C_4$, $C_5$, and $C_6$ cycloalkyl groups "Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent only stable compounds are envisioned for this invention.

"Therapeutically effective amount" is intended to include an amount of a compound of the present invention alone or an amount of the combination of compounds claimed or an amount of a compound of the present invention in combination with other active ingredients effective to treat the inflammatory diseases described herein.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

The compounds of Formula I can be prepared using the reactions and techniques described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1999).

EXAMPLES

The compounds of this invention and their preparation can be understood further by the following working examples. These examples are meant to be illustrative of the present invention, and are not to be taken as limiting thereof.

Example 1

Part A. Preparation of 3-Bromo-5-nitrobenzoic Acid

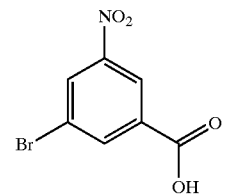

3-Nitrobenzoic acid (16.7 g, 100 mmol, 1 equiv.) was stirred in 50 ml of trifluoroacetic and 20 ml of sulfuric at at 50° C. Added N-Bromosuccinimde (26.7 g, 150 mmol, 1.5 equiv.) in 3 portions over 3 hours. Stirred for 16 hours then cooled to 25° C. Poured the reaction into 200 ml of ice water and extracted with ethyl acetate (3×100 ml). The organic layers were combined, dried over $Na_2SO_4$, and stripped in vacuo to give a white solid. Purified by recrystallization in methylene chloride to give 17.7 g of a white solid as product. NMR (300 MHz, DMSO-$d_6$) δ 14.30–13.30 (m, 1H), 8.60 (t, 1H, J=3 Hz), 8.55 (s, 1H, J=3 Hz), 8.37 (s, 1H, J=3 Hz).

Part B. Preparation of 3-bromo-N-methyl-5-nitrobenzamide

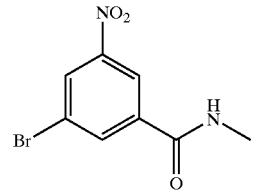

3-bromo-N-methyl-5-nitrobenzamide was prepared by the procedures found in Example 3, parts A and B. starting with 3-bromo-5-nitrobenzoic acid from Example 1, part A. NMR (300 MHz, DMSO-$d_6$) δ 9.92 (m, 1H), 8.64 (s, 1H), 8.53 (s, 1H), 8.43 (s, 1H), 2.81 (d, 3H, J=7 Hz).

Part C. Preparation of 5-(3-bromo-5-nitrophenyl)-1-methyl-1H-tetraazole

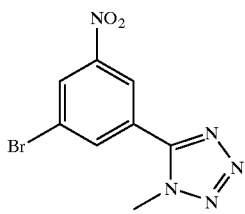

The following work was done behind a blast shield in a well ventilated hood. 3-bromo-N-methyl-5-nitrobenzamide (23.20 g, 90 mmol, 1 equiv.) was suspended in 200 ml of acetonitrile at 25° C. under nitrogen then sodium azide (5.82 g, 90 mmol, 1 equiv.) was added. Cooled to 0° C. then very slowly added triflic anhydride (15.07 ml, 90 mmol, 1 equiv.) dropwise via an addition funnel. The reaction became an amber solution. Worked up after 4 hours by adding 200 ml of sat'd NaHCO$_3$ and stirred 10 minutes. Then added ethyl acetate and separated the layers. The ethyl acetate was rinsed twice with sat'd NaHCO$_3$ then once with brine. The ethyl acetate was dried over MgSO4 then stripped in vacuo to give a dark amber oil which was stirred in 25 ml of ethyl acetate. After stirring 5 minutes, solids which precipitated were filtered off, and pumped under high vacuum to give 10.5 g of tan solids. The filtrate was stripped then purified over silica gel in 100% methylene chloride to obtain an additional 9.0 g of solids. By NMR both solids were identical for product and were combined. NMR (300 MHz, CDCl$_3$) δ 8.60 (s, 1H), 8.55 (s, 1H), 8.32 (s, 1H), 7.26 (s, 1H), 4.29 (s, 3H).

Part D. Preparation of 1-methyl-5-(3-nitro-5-vinylphenyl)-1H-tetraazole

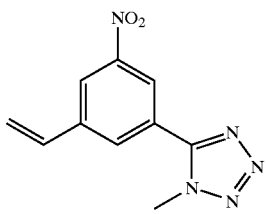

5-(3-bromo-5-nitrophenyl)-1-methyl-1H-tetraazole from Part C (19.50 g, 68.6 mmol, 1 equiv.), tributylvinyl tin (Aldrich, 20.06 ml, 68.6 mmol, 1 equiv.), and tetrakis (triphenylphosphine)palladium(0)(Aldrich, 1.59 g, 1.37 mmol, 0.02 equiv.) were mixed at 25° C. under nitrogen then refluxed for 2 hours. Worked up by stripping the reaction then purified over silica gel in 100% methylene chloride to 1:1 methylene chloride/ethyl acetate. Obtained 22.0 g of product and a tributyltin impurity. NMR of product (300 MHz, CDCl$_3$) δ 8.49 (d, 2H, J=7 Hz), 8.19 (s, 1H), 6.86 (m, 1H), 6.05 (d, 1H, J=15 Hz), 5.60 (d, 1H, J=7 Hz), 4.28 (s, 3H).

Part E. Preparation of 3-ethyl-5-(1-methyl-1H-tetraazol-5-yl)aniline

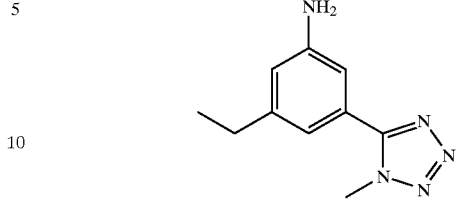

Pd(OH)$_2$(3.0 g) was carefully wetted down under nitrogen with methanol then 1-methyl-5-(3-nitro-5-vinylphenyl)-1H-tetraazole (17.0 g) dissolved in 50 ml of methanol was added. Hydrogenated at 50 PSI for 4 hours. Worked up by filtering the reaction under nitrogen through fiberglass filter paper. The filtrate was stripped in vacuo to give 14.3 g of amber solids as product. NMR (300 MHz, CDCl$_3$) δ 6.90 (s, 1H), 6.87 (s, 1H), 6.73 (s, 1H), 4.16 (s, 3H), 3.95 (bs, 2H), 2.65 (q, 2H, J=7 Hz), 1.22 (t, 3H, J=7 Hz).

Part F. Preparation of phenyl 3-ethyl-5-(1-methyl-1H-tetraazol-5-yl)phenylcarbamate

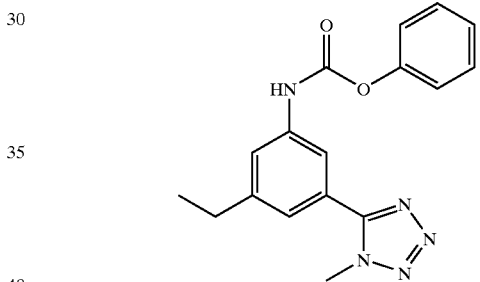

3-ethyl-5-(1-methyl-1H-tetraazol-5-yl)aniline (3.83 g, 19 mmol, 1 equiv.), was dissolved in THF at 25° C. under nitrogen then 2,6-lutidine (Aldrich, 2.17 ml, 19 mmol, 1 equiv.) was added. Cooled the reaction to 0° C. Added a THF solution of phenyl chloroformate (2.36 ml, 19 mmol, 1 equiv.) dropwise via an addition funnel. Worked up after 1 hour by adding ethyl acetate and 0.1 N HCl. Separated the layers and rinsed the organic layer twice more with 0.1 N HCl and once with brine. The organic layer was dried over MgSO$_4$ then stripped in vacuo to give 6.00 g of tan solids as product. NMR (300 MHz, CDCl$_3$) δ 7.86 (s, 1H), 7.50–7.30 (m, 5H), 7.30–7.10 (m, 3H), 4.17 (s, 3H), 2.71 (q, 2H, J=7 Hz), 1.27 (t, 3H, J=7 Hz).

Part G. Preparation of (3S)-1-[(2E)-2-butenoyl]-3-(4-fluorobenzyl)piperidine

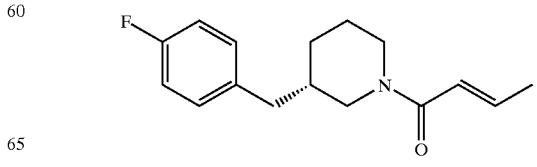

(S)-3-(4-fluorobenzyl)piperidine (4.00 g, 20.7 mmol, 1 equiv.), as prepared in WO 00/35453, which is hereby incorporated by reference, crotonic acid (1.78 g, 20.7 mmol, 1 equiv.), and benzotriazol-1-yloxytripyrrolidinophosphonium hexafluorophosphate (PyBOP, 11.85 g, 22.8 mmol, 1.1 equiv.) were mixed at 0° C. under nitrogen then triethylamine (5.77 mL, 41.4 mmol, 2 equiv.) was added. Worked up after 20 hours by stripping off the solvent in vacuo then purifying over silica gel in 3:1 to 1:1 hexanes/ethyl acetate to obtain 5.40 g of a colorless oil as product. NMR (300 MHz, CDCl$_3$) δ 7.20–7.04 (m, 2H), 7.04–6.90 (m, 2H), 6.90–6.60 (m, 1H), 6.40–6.00 (m, 1H), 4.00–3.60 (m, 1H), 3.10–2.30 (m, 5H), 1.95–1.60 (m, 6H), 1.60–1.30 (m, 1H), 1.30–1.00 (m, 1H).

Part H. Preparation of (2R,3R)-3-{benzyl[(1R)-1-phenylethyl]amino}-1-[(3S)-3-(4-fluorobenzyl)piperidin-1-yl]-1-oxobutan-2-ol

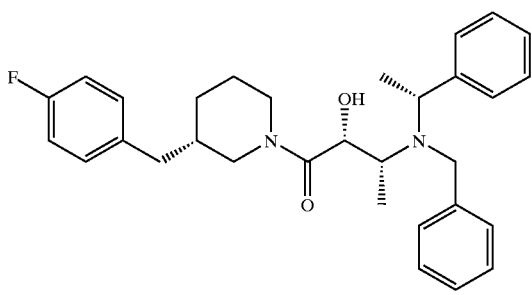

To a flame dried 3-neck flask under nitrogen was added (R)-(+)—N-Benzyl-α-methylbenzylamine (Aldrich, 6.92 ml, 33.1 mmol, 1.6 equiv.) in 50 ml of THF then cooled to −10° C. A solution of 1.6 M n-Butyllithium in hexanes (19.37 ml, 31 mmol, 1.5 equiv.) was added dropwise keeping the temperature below 0° C. Stirred the pink solution for 45 minutes then cooled further to −70° C. then added dropwise (3S)-1-[(2E)-2-butenoyl]-3-(4-fluorobenzyl)piperidine (5.40 g, 20.7 mmol, 1 equiv.). Stirred at −70° C. for 1.5 additional hours then added (1S)-(+)-(10-Camphorsulfonyl)oxaziridine (Aldrich, 7.58 g, 33.1 mmol, 1.6 equiv.) in 1 portion neat. Stirred for 1 hour at −70° C. then allowed to warm to 0° C. Quenched with 50 ml of sat'd NH$_4$Cl. Extracted 3 times with methylene chloride. The organic layers were combined, dried over MgSO$_4$ then stripped in vacuo to give an oil which was purified over silica gel in 100% chloroform to 9:1 chloroform/ethyl acetate. Obtained an oil which was stirred in Et$_2$O. Solids formed which were filtered off. The filtrate was stripped in vacuo to give 6.13 g of a white glass as product. NMR (300 MHz, CDCl$_3$) δ 7.60–7.40 (m, 4H), 7.40–7.10 (m, 5H), 7.10–6.80 (m, 5H), 4.60–4.10 (m, 6H), 4.00–3.85 (m, 1H), 3.85–3.70 (m, 1H), 3.00–2.70 (m, 1H), 2.70–2.50 (m, 1H), 2.50–2.20 (m, 3H), 2.00–1.80 (m, 1H), 1.70–1.20 (m, 4H), 1.01 (d, 3H, J=7 Hz), 0.80–0.50 (m, 1H).

Part I. Preparation of (2S,3R)-3-{benzyl[(1R)-1-phenylethyl]amino}-1-[(3S)-3-(4-fluorobenzyl)piperidin-1-yl]butan-2-ol

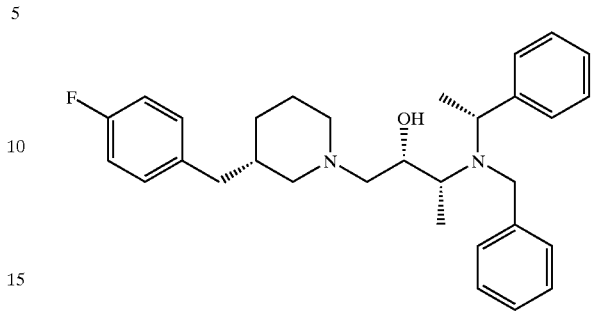

(2R,3R)-3-{benzyl[(1R)-1-phenylethyl]amino}-1-[(3S)-3-(4-fluorobenzyl)piperidin-1-yl]-1-oxobutan-2-ol (1.00 g, 2.05 mmol, 1 equiv.) was dissolved in THF at 25° C. under nitrogen then 1.0 M Borane in THF (6.14 ml, 6.14 mmol, 3 equiv.) was added dropwise. Foaming and gas evolution were observed along with a slight exotherm. Refluxed for 3 hours. Stopped heating. Carefully quenched with the dropwise addition of 10 ml of methanol. Once the addition was complete, added 1 N HCl and refluxed for 4 hours. Worked up by carefully basifying with sat'd NaHCO$_3$. The basic aqueous was then extracted 3 times with chloroform. The organic layers were combined, dried over MgSO$_4$ and stripped in vacuo to give 600 mg of a colorless oil as product. NMR (300 MHz, CDCl$_3$) δ 7.45–7.10 (m, 10H), 7.10–6.97 (m, 2H), 6.97–6.80 (m, 2H), 4.00–3.80 (q, 1H, J=7 Hz), 3.40–3.20 (m, 1H), 2.75–2.55 (m, 2H), 2.55–2.20 (m, 3H), 2.05 (t, 1H, J=7 Hz), 1.70–1.37 (m, 9H), 1.37 (d, 3H, J=7 Hz), 1.20 (d, 3H, J=7 Hz), 1.00–0.70 (m, 1H).

Part J. Preparation of (2S,3R)-3-amino-1-[(3S)-3-(4-fluorobenzyl)-1-piperidinyl]-2-butanol

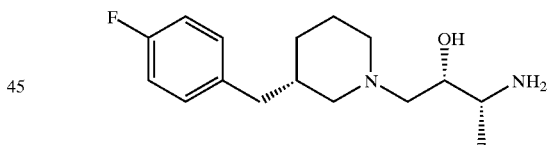

Pd(OH)$_2$ was carefully wetted down under nitrogen with methanol then (2S,3R)-3-{benzyl[(1R)-1-phenylethyl]amino}-1-[(3S)-3-(4-fluorobenzyl)piperidin-1-yl]butan-2-ol (5.10 g) dissolved in 50 ml of methanol was added followed by 50 ml of acetic acid. Hydrogenated at 50 PSI overnight. Worked up by filtering off the catalyst through fiberglass filter paper under nitrogen. The filtrate was stripped in vacuo to give an oil which was dissolved in methylene chloride then rinsed twice with saturated NaHCO$_3$. The aqueous was adjusted to 12 with 1 N NaOH then extracted 3 times with methylene chloride. The methylene chloride extracts from the 1 N NaOH aqueous work up were combined, dried over MgSO$_4$ then stripped in vacuo to give 2.6 g of a near-colorless oil as product. NMR (300 MHz, CDCl$_3$) δ 7.15–7.00 (m, 2H), 7.00–6.85 (m, 2H), 3.60–3.40 (m, 1H), 3.10–2.90 (m, 1H), 2.90—2.80 (m, 1H), 2.80–2.60 (m, 1H), 2.60–2.00 (m, 5H), 2.00–1.40 (m, 7H), 1.06 (d, 3H, J=7 Hz), 1.00–0.80 (m, 1H).

Part K. Preparation of N-[3-ethyl-5-(1-methyl-1H-tetraazol-5-yl)phenyl]-N'-{(1R,2S)-3-[(3S)-3-(4-fluorobenzyl)-1-piperidinyl]-2-hydroxy-1-methylpropyl}urea

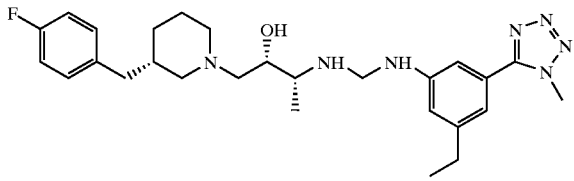

(2S,3R)-3-amino-1-[(3S)-3-(4-fluorobenzyl)-1-piperidinyl]-2-butanol (50 mg, 0.189 mmol, 1 equiv.) and phenyl 3-ethyl-5-(1-methyl-1H-tetraazol-5-yl)phenylcarbamate (58 mg, 0.189 mmol, 1 equiv.) were stirred together in acetonitrile under nitrogen at 25° C. Worked up after 6 hours by stripping off the solvent in vacuo then purifying over silica gel in 100% ethyl acetate to 4:1 chloroform/methanol. Obtained 69 mg of a white glass as product. NMR (300 MHz, CDCl$_3$) δ 7.67 (s, 1H), 7.45 (m, 1H), 7.13 (m, 1H), 7.10–7.00 (m, 2H), 7.00–6.80 (m, 2H), 4.12 (s, 3H), 4.00–3.82 (m, 1H), 3.82–3.60 (m, 1H), 3.00–2.85 (m, 1H), 2.85–2.68 (m, 1H), 2.61 (q, 2H, J=7 Hz), 2.60–2.20 (m, 6H) 1.90–1.40 (m, 5H), 1.30–1.10 (m, 5H), 1.00–0.80 (m, 1H) Mass Spec (ESI) detects 510 (M+H).

Example 2

Part A. Preparation of phenyl 3-(1-methyl-1H-tetraazol-5-yl)phenylcarbamate

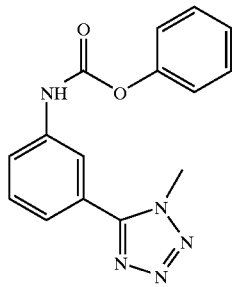

Phenyl 3-(1-methyl-1H-tetraazol-5-yl)phenylcarbamate was made starting from 3-nitrobenzoic acid using the procedures found in Example 1, parts B, C, F. NMR (300 MHz, DMSO-d$_6$) δ 10.60 (bs, 1H), 8.03 (s, 1H), 7.80–7.70 (m, 1H), 7.60–7.50 (m, 2H), 7.50–7.35 (m, 2H), 7.35–7.20 (m, 3H), 4.17 (s, 3H).

Part B. Preparation of N-{(1R,2S)-3-[(3S)-3-(4-fluorobenzyl)-1-piperidinyl]-2-hydroxy-1-methylpropyl}-N'-[3-(1-methyl-1H-tetraazol-5-yl)phenyl]urea

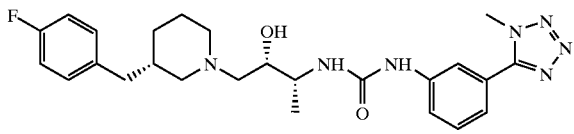

(2S,3R)-3-amino-1-[(3S)-3-(4-fluorobenzyl)-1-piperidinyl]-2-butanol (50 mg, 0.189 mmol, 1 equiv.) and phenyl 3-(1-methyl-1H-tetraazol-5-yl)phenylcarbamate (53 mg, 0.189 mmol, 1 equiv.) were stirred together in acetonitrile under nitrogen at 25° C. Worked up after 6 hours by stripping off the solvent in vacuo then purifying over silica gel in 100% ethyl acetate to 4:1 chloroform/methanol. Obtained 58 mg of a white glass as product. NMR (300 MHz, CDCl$_3$) δ 7.84 (S, 1 h), 7.61 (D, 1 h, j=7 Hz), 7.39 (t, 1H, J=7 Hz), 7.28 (d, 1H, J=7 Hz), 7.15–7.00 (m, 2H), 7.00–6.80 (m, 2H), 4.17 (s, 3H), 4.00–3.84 (m, 1H), 3.84–3.70 (m, 1H), 2.88 (d, 1H, J=7 Hz), 2.80–2.60 (m, 1H), 2.60–2.10 (m, 5H), 1.80–1.40 (m, 5H), 1.14 (s, 3H), 1.05–0.80 (m, 1H). Mass Spec (ESI) detects 482 (M+H).

Example 3

Part A. Preparation of methyl 3-(chlorocarbonyl)-5-nitrobenzoate

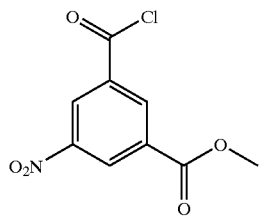

Mono-methyl-5-nitroisophthalate (10.0 g, 39.19 mmol) and oxalyl chloride (39.2 ml of a 2.0 M solution in CH$_2$Cl$_2$, 78.38 mmol) were combined in 100 ml CH$_2$Cl$_2$, and a few drops of DMF were added, causing vigorous gas evolution. The mixture was stirred for 2 hours at room temperature, during which time the suspension became a clear solution. Concentrated in vacuo, then reconcentrated in vacuo twice from 200 ml toluene to remove excess oxalyl chloride. Used immediately in the next step.

Part B. Preparation of methyl 3-[(methylamino)carbonyl]-5-nitrobenzoate

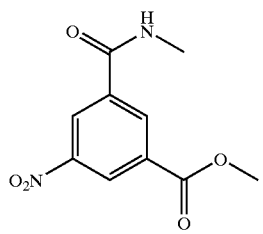

A solution of methylamine (120 mmol, 3 eq.) in 100 ml THF was cooled to 0° C. A solution of crude methyl 3-(chlorocarbonyl)-5-nitrobenzoate from the previous step (entire amount) in 100 ml THF was added dropwise, causing a white solid to precipitate. The mixture was allowed to come to room temperature, and stirred for 16 hours. The solids were removed by filtration, and rinsed with THF. The filtrate was concentrated in vacuo to yield a white solid which was triturated with diethyl ether, collected by filtration, and dried to yield 10.11 g of a white solid as product. NMR (300 MHz, DMSO) δ 9.05 (bd, 0.7H, J=4 Hz), 8.94 (bd, 0.3H, J=4 Hz), 8.90 (dd, 1H, J=2 Hz), 8.81–8.77 (m, 1H), 8.74–8.72 (m, 1H), 3.96 (s, 3H), 2.84 (d, 3H, J=4 Hz).

Part C. Preparation of methyl 3-(1-methyl-1H-tetraazol-5-yl)-5-nitrobenzoate

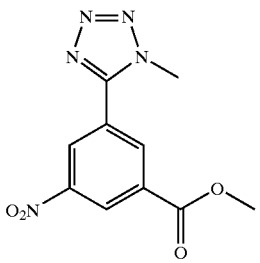

The following work was done behind a blast shield in a well ventilated hood. Methyl 3-[(methylamino)carbonyl]-5-nitrobenzoate (10.1 g, 42.4 mmol) and sodium azide (2.9 g, 44.6 mmol) were suspended in dry acetonitrile under nitrogen, the mixture was cooled to −5° C., and triflic anhydride (7.5 ml, 44.6 mmol) was added slowly via syringe. The mixture was stirred at −5° C. for 1.5 h, during which time it became a clear solution. The reaction was worked up by adding 200 ml 1 N NaOH, and stirring for ten minutes. The layers were then separated, and the aqueous was extracted with 3×100 ml CH$_2$CO$_2$. The combined organic phases were concentrated in vacuo, then taken up in 300 ml CH$_2$Cl$_2$ and washed with 100 ml 1 N NaOH, 3×50 ml water, and 50 ml brine. The organic phase was dried over Na$_2$SO$_4$, then concentrated to a yellow oil. This was purified over SiO$_2$, eluting with 5–10% EtOAc/CH$_2$Cl$_2$, to yield 8.1 g of a colorless oil, which solidified upon standing, as product. NMR (300 MHz, DMSO) δ 8.90 (dd, 1H, J=2 Hz), 8.80 (dd, 1H, J=2 Hz), 8.73 (dd, 1H, J=2 Hz), 4.21 (s, 3H), 3.98 (s, 3H).

Part D. Preparation of methyl 3-amino-5-(1-methyl-1H-tetraazol-5-yl)benzoate

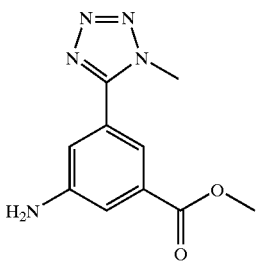

Methyl 3-(1-methyl-1H-tetraazol-5-yl)-5-nitrobenzoate (435 mg, 1.65 mmol), palladium on activated carbon (10%) (50 mg), and 1:1 EtOAc/MeOH (20 ml) were hydrogenated at 50 PSI for 3 hours. The catalyst was removed by filtering through fiberglass filter paper under nitrogen and rinsed with MeOH. The filtrate was concentrated in vacuo to yield 370 mg of white solids as product. NMR (300 MHz, DMSO) δ 7.49 (dd, 1H, J=2 Hz), 7.41 (dd, 1H, J=2 Hz), 7.25 (dd, 1H, J=2 Hz), 5.83 (s, 2H), 4.15 (s, 3H), 3.85 (s, 3H).

Part E. Preparation of [3-amino-5-(1-methyl-1H-tetraazol-5-yl)phenyl]methanol

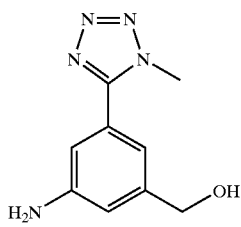

Methyl 3-amino-5-(1-methyl-1H-tetraazol-5-yl)benzoate (1 g, 4.29 mmol) was suspended in 20 ml THF, and the mixture was cooled to 0° C. To this mixture, LAH (4.3 ml of a 1.0 M solution in THF, 4.3 mmol) was added dropwise, causing the mixture to turn first green, then purple. The mixture was allowed to come to room temperature and stirred for 16 hours, during which the color changed to amber. The reaction was quenched using the Steinhardt procedure (Feiser & Feiser, Reagents for Organic Synthesis vol. 1, 1967, pg. 584.), the resulting solids were removed by filtration, rinsed with EtOAc, and the filtrate was concentrated in vacuo to yield 900 mg of pale yellow solids as product. NMR (300 MHz, DMSO) δ 6.88–6.87 (m, 2H), 6.77 (s, 1H), 5.43 (bs, 2H), 5.18 (t, 1H, J=6 Hz), 4.44 (d, 2H, J=6 Hz), 4.13 (s, 3H).

Part F. Preparation of 3-methyl-5-(1-methyl-1H-tetraazol-5-yl)aniline

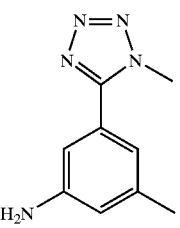

[3-amino-5-(1-methyl-1H-tetraazol-5-yl)phenyl]methanol (300 mg, 1.46 mmol), palladium on activated carbon (10%) (100 mg), a few drops of concentrated HCl, and 20 ml MeOH were hydrogenated at 50 PSI for 16 hours. The mixture was made alkaline by the addition 10% NaOH (aq) (5 ml), and the catalyst was removed by filtering through fiberglass filter paper under nitrogen. The filtrate was concentrated in vacuo, the residue was partitioned between 50 ml EtOAc and 50 ml water, and the layers were separated. The aqueous was extracted with 2×25 ml EtOAc, and the combined organic phases were dried (Na$_2$SO$_4$) and concentrated in vacuo to yield 270 mg of tan solids as product. NMR (300 MHz, DMSO) δ 6.81 (s, 1H), 6.75 (s, 1H), 6.60 (s, 1H), 5.37 (bs, 2H), 4.12 (s, 3H), 2.25 (s, 3H).

Part G. Preparation of Phenyl 3-methyl-5-(1-methyl-1H-tetraazol-5-yl)phenylcarbamate

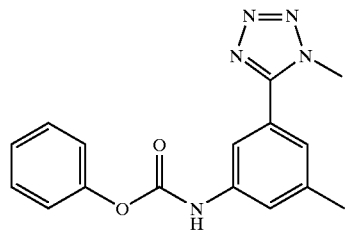

Phenyl 3-methyl-5-(1-methyl-1H-tetraazol-5-yl)phenylcarbamate was prepared from 3-methyl-5-(1-methyl-1H-tetraazol-5-yl)aniline via the procedure in part F of example 1. The product was 85% pure by NMR. Used as is in the next step. NMR (300 MHz, DMSO) δ 10.47 (s, 1H), 7.84 (s, 1H), 7.57 (s, 1H), 7.47–7.38 (m, 3H), 7.30–7.23 (m, 3H), 4.17 (s, 3H), 2.40 (s, 3H).

Part H. Preparation of N-{(1R,2S)-3-[(3S)-3-(4-fluorobenzyl)-1-piperidinyl]-2-hydroxy-1-methylpropyl}1-N'-[3-methyl-5-(1-methyl-1H-tetraazol-5-yl)-phenyl]urea

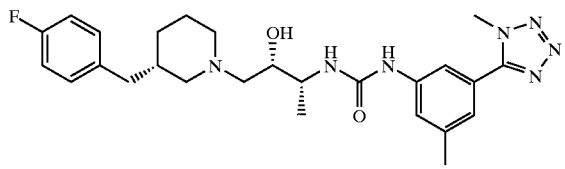

N-{(1R,2S)-3-[(3S)-3-(4-fluorobenzyl)-1-piperidinyl]-2-hydroxy-1-methylpropyl}-N'-[3-methyl-5-(1-methyl-1H-tetraazol-5-yl)phenyl]urea was prepared from Phenyl 3-methyl-5-(1-methyl-1H-tetraazol-5-yl)phenylcarbamate and (2S,3R)-3-amino-1-[(3S)-3-(4-fluorobenzyl)-1-piperidinyl]-2-butanol via the procedure in part K of example 1. NMR (300 MHz, DMSO) δ 7.72 (s, 1H), 7.34 (s, 1H), 7.21 (s, 1H), 7.13 (dd, 2H, J=9, 8 Hz), 6.93 (dd, 2H, J=9 Hz), 4.18 (s, 3H), 3.80–3.71 (m, 2H), 2.93–2.81 (m, 2H), 2.48 (d, 2H, J=7 Hz), 2.44–2.31 (m, 5H), 2.05 (dd, 1H, J=10, 11 Hz), 1.83–1.53 (m, 5H), 1.11 (d, 3H, J=7 Hz), 1.05–0.94 (m, 1H). Mass spec (ESI+) detects 496 (M+H).

Utility

The utility of the compounds in accordance with the present invention as inhibitors of the migration of eosinophils or cell lines expressing the chemokine receptors may be demonstrated by methodology known in the art, such as the chemotaxis assay disclosed by Bacon et al., Brit. J. Pharmacol., 95, 966–974 (1988). In particular, the compound of the present invention have activity in inhibition of the migration of eosinophils in the aforementioned assays. As used herein, "activity" is intended to mean a compound demonstrating an IC50 of 10 μM or lower in concentration when measured in the aforementioned assays. Such a result is indicative of the intrinsic activity of the compounds as modulators of chemokine receptor activity. A human eosinophil chemotaxis assay protocol is described below.

Human Eosinophil Chemotaxis Assay

Neuroprobe MBA96 96-well chemotaxis chambers with Neuroprobe polyvinylpyrrolidone-free polycarbonate PFD5 5-micron filters in place are warmed in a 37° C. incubator prior to assay. Freshly isolated human eosinophils, isolated according to a method such as that described by Hansel et al. (1991), are suspended in RPMI 1640 with 0.1% bovine serum albumin at 1×10⁶ cells/ml and warmed in a 37° C. incubator prior to assay. A 20 nM solution of human eotaxin in RPMI 1640 with 0.1% bovine serum albumin is warmed in a 37° C. incubator prior to assay. The eosinophil suspension and the 20 nM eotaxin solution are each mixed 1:1 with prewarmed RPMI 1640 with 0.1% bovine serum albumin with or without a dilution of a test compound that is at two fold the desired final concentration. These mixtures are warmed in a 37° C. incubator prior to assay. The filter is separated from the prewarmed Neuroprobe chemotaxis chamber and the eotaxin/compound mixture is placed into a Polyfiltronics MPC 96 well plate that has been placed in the bottom part of the Neuro Probe chemotaxis chamber. The approximate volume is 370 microliters and there should be a positive meniscus after dispensing. The filter is replaced above the 96 well plate, the rubber gasket is attached to the bottom of the upper chamber, and the chamber assembled. A 200 μl volume of the cell suspension/compound mixture is added to the appropriate wells of the upper chamber. The upper chamber is covered with a plate sealer, and the assembled unit placed in a 37° C. incubator for 45 minutes. After incubation, the plate sealer is removed and all remaining cell suspension is aspirated off. The chamber is disassembled and, while holding the filter by the sides at a 90-degree angle, unmigrated cells are washed away using a gentle stream of phosphate buffered saline dispensed from a squirt bottle and then the filter wiped with a rubber tipped squeegee. The filter is allowed to completely dry and immersed completely in Wright Giemsa stain for 30–45 seconds. The filter is rinsed with distilled water for 7 minutes, rinsed once with water briefly, and allowed to dry. Migrated cells are enumerated by microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited. For example, eosinophilic infiltration to inflammatory sites (e.g., in asthma or allergic rhinitis) can be inhibited according to the present method. In particular, the compound of the following examples has activity in blocking the migration of cells expressing the CCR-3 receptor using the appropriate chemokines in the aforementioned assays. As used herein, "activity" is intended to mean a compound demonstrating an IC50 of 10 μM or lower in concentration when measured in the aforementioned assays. Such a result is also indicative of the intrinsic activity of the compounds as modulators of chemokine receptor activity.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease, solid organ transplantation; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs; nasal polyposis interstitial nephritis; and endometriosis. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV, including HIV infection and HIV neuropathogenesis.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., Toxocara), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases. In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) non-steroidal antiinflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (I) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (1) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

It is desirable to find new compounds with improved pharmacological characteristics compared with known CCR-3 inhibitors. For example, it is desirable to find new compounds with improved CCR-3 inhibitory activity and selectivity for CCR-3 versus other G protein-coupled receptors (i.e. 5HT2A receptor). It is also desirable to find compounds with advantageous and improved characteristics in one or more of the following categories:

(a) pharmaceutical properties (i.e. solubility, permeability, amenability to sustained release formulations); (b) dosage requirements (e.g., lower dosages and/or once-daily dosing); (c) factors which decrease blood concentration peak-to-trough characteristics (i.e. clearance and/or volume of distribution); (d) factors that increase the concentration of active drug at the receptor (i.e. protein binding, volume of distribution); (e) factors that decrease the liability for clinical drug-drug interactions (cytochrome P450 enzyme inhibition or induction, such as CYP 2D6 inhibition, see G K Dresser, J D Spence, D G Bailey Clin. Pharmacokinet. 2000, 38, 41–57, which is hereby incorporated by reference); (f) factors that decrease the potential for adverse side-effects (i.e. pharmacological selectivity beyond G protein-coupled receptors, potential chemical or metabolic reactivity, limited CNS penetration) (g) factors that improve manufacturing costs or feasibility (i.e. difficulty of synthesis, number of chiral centers, chemical stability, ease of handling).

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the inflammatory disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

As will be apparent to one skilled in the art, numerous modifications and variations of the present invention are possible in light of the above teachings. It is therefore to be understood that within the scope of the appended claims, the invention may be practiced otherwise than as specifically described herein.

What is claimed is:

1. A compound of formula (I):

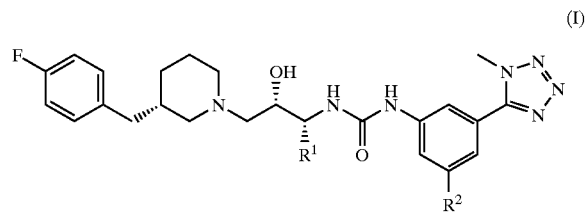

or a pharmaceutically acceptable salt form thereof, wherein
$R^1$ is selected from methyl; and
$R^2$ is selected from H, methyl, and ethyl.

2. A compound of claims 1, wherein
$R^2$ is H.

3. A compound of claims 1, wherein
$R^2$ is methyl.

4. A compound of claims 1, wherein
$R^2$ is ethyl.

5. A compound of claim 1 or a pharmaceutically acceptable salt, wherein the compound is selected from:
N-[3-ethyl-5-(1-methyl-1H-tetraazol-5-yl)phenyl]-N'-{(1R,2S)-3-[(3S)-3-(4-fluorobenzyl)-1-piperidinyl]-2-hydroxy-1-methylpropyl}urea;
N-{(1R,2S)-3-[(3S)-3-(4-fluorobenzyl)-1-piperidinyl]-2-hydroxy-1-methylpropyl}-N'-[3-(1-methyl-1H-tetraazol-5-yl)phenyl]urea; and
N-{(1R,2S)-3-[(3S)-3-(4-fluorobenzyl)-1-piperidinyl]-2-hydroxy-1-methylpropyl}-N'-[3-methyl-5-(1-methyl-1H-tetraazol-5-yl)phenyl]urea.

6. A pharmaceutical composition comprising a pharmaceutically acceptable carrier and a therapeutically effective amount of a compound according to claim 1, or a pharmaceutically acceptable salt thereof.

7. A method for treating asthma, comprising administering to a patient in need thereof a therapeutically effective amount of a compound according to claim 1.

* * * * *